United States Patent
Spence et al.

(10) Patent No.: US 9,677,178 B2
(45) Date of Patent: Jun. 13, 2017

(54) ALKOXYAMINOSILANE COMPOUNDS AND APPLICATIONS THEREOF

(71) Applicant: AIR PRODUCTS AND CHEMICALS, INC., Allentown, PA (US)

(72) Inventors: Daniel P. Spence, Carlsbad, CA (US); Xinjian Lei, Vista, CA (US); Ronald Martin Pearlstein, San Marcos, CA (US); Manchao Xiao, San Diego, CA (US); Richard Ho, Anaheim, CA (US)

(73) Assignee: VERSUM MATERIALS US, LLC, Allentown, PA (US)

( * ) Notice: Subject to any disclaimer, the term of this patent is extended or adjusted under 35 U.S.C. 154(b) by 23 days.

(21) Appl. No.: 14/940,249

(22) Filed: Nov. 13, 2015

(65) Prior Publication Data

US 2016/0083847 A1    Mar. 24, 2016

Related U.S. Application Data

(63) Continuation-in-part of application No. 13/745,102, filed on Jan. 18, 2013, now Pat. No. 9,200,167.

(60) Provisional application No. 61/591,318, filed on Jan. 27, 2012.

(51) Int. Cl.
| | |
|---|---|
| *C07F 7/10* | (2006.01) |
| *C07F 7/18* | (2006.01) |
| *C23C 16/50* | (2006.01) |
| *C23C 16/455* | (2006.01) |
| *C09D 7/12* | (2006.01) |

(52) U.S. Cl.
CPC .............. *C23C 16/50* (2013.01); *C07F 7/10* (2013.01); *C07F 7/188* (2013.01); *C07F 7/1868* (2013.01); *C07F 7/1888* (2013.01); *C09D 7/1233* (2013.01); *C23C 16/45525* (2013.01)

(58) Field of Classification Search
CPC .......... C07F 7/10; C07F 7/188; C07F 7/1868; C07F 7/1888; C23C 16/45525; C23C 16/50; C09D 7/1233
USPC .......... 556/410; 427/248.1, 578; 106/287.11, 106/287.16
See application file for complete search history.

(56) References Cited

U.S. PATENT DOCUMENTS

| | | | |
|---|---|---|---|
| 4,345,088 A | 8/1982 | Vick et al. | |
| 4,471,132 A | 9/1984 | Hallgren | |
| 4,491,669 A * | 1/1985 | Arkles | C07F 7/025 528/31 |
| 4,515,932 A * | 5/1985 | Chung | C08G 77/08 528/12 |
| 4,739,088 A * | 4/1988 | Endres | C07F 7/1868 556/411 |
| 6,114,558 A | 9/2000 | Larson et al. | |
| 7,425,350 B2 | 9/2008 | Todd | |
| 7,524,735 B1 | 4/2009 | Gauri et al. | |
| 7,582,555 B1 | 9/2009 | Lang et al. | |
| 7,629,227 B1 | 12/2009 | Wang et al. | |
| 7,875,312 B2 | 1/2011 | Thridandam et al. | |
| 7,888,233 B1 | 2/2011 | Guari et al. | |
| 7,888,273 B1 | 2/2011 | Wang et al. | |
| 7,915,139 B1 | 3/2011 | Lang et al. | |
| 7,943,531 B2 | 5/2011 | Nemani et al. | |
| 8,187,951 B1 * | 5/2012 | Wang | H01L 21/76224 257/E21.559 |
| 8,937,141 B2 * | 1/2015 | Sumi | C08K 5/0091 524/127 |
| 2002/0180028 A1 | 12/2002 | Borovik et al. | |

(Continued)

FOREIGN PATENT DOCUMENTS

| | | |
|---|---|---|
| CN | 1049014 | 2/1991 |
| CN | 1356181 | 7/2002 |

(Continued)

OTHER PUBLICATIONS

J. Pikies, et al, Elektronische und sterische Effekte in 29Si-NMR-Spektren von Amino-substituierten Silanen, Z. anorg. allg. Chem., 521, 1985, 173-182.
J. Pikies, et al, Darstellung und spektroskopische Eigenschaften von Alkoxyaminosilanen (RO)nMe3-nSiNHC6HX, Z. anorg. allg. Chem., 503, 1983, 224-230.
W. Ando, et al, Photolysis of Diazidosilanes. Generation and Reactions of Digonal Silicon Intermediates such as Silacarbodiimides, J.C.S. Chem. Comm., 1981, 597-598.
J. G. Radziszewski, Multiply Bonded Silicon: Martrix Isolation and Chemical Trapping of Products of Pyrolysis and Photolysis of Triazidophenylsilane, Organomettalics, 1993, 12, 4816-4824.
J. Pikies, Si-Chemische Verschiebungen in Alkoxy(amino)silanen, Z. anorg. allg. Chem., 1983, 498, 218-224.

(Continued)

*Primary Examiner* — Porfirio Nazario Gonzalez
(74) *Attorney, Agent, or Firm* — Michael K. Boyer

(57) ABSTRACT

Alkoxyaminosilane compound having formula I, and processes and compositions for depositing a silicon-containing film, are described herein:

$(R^1R^2)NSiR^3OR^4OR^5$    Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group.

10 Claims, No Drawings

(56) References Cited

U.S. PATENT DOCUMENTS

| | | |
|---|---|---|
| 2009/0104791 A1 | 4/2009 | Nemani et al. |
| 2010/0190942 A1 | 7/2010 | Hosaka et al. |

FOREIGN PATENT DOCUMENTS

| | | |
|---|---|---|
| CN | 101802984 | 8/2010 |
| EP | 1062220 | 4/2006 |
| GB | 2138013 | 10/1984 |
| JP | S57175195 | 10/1982 |
| JP | 62502613 | 8/1987 |
| JP | 64500031 | 1/1989 |
| JP | H07109304 | 4/1995 |
| JP | H08120021 | 5/1996 |
| JP | 2002534527 | 10/2002 |
| JP | 2007051363 | 3/2007 |
| JP | 2007318142 | 12/2007 |
| KR | 10200900332200 | 4/2009 |
| WO | 0042049 | 7/2000 |
| WO | 0157099 | 8/2001 |
| WO | 2005082952 | 9/2005 |

OTHER PUBLICATIONS

Y. H. Chang, "Investigation of Thermally Induced a-Deoxysilylation of Organosilylated Hydroxylamine Derivatives as a General Method for Nitrene Production", J. Org. Chem., 1981, 342-354.

Larry L. Hence, et al, The Sol-Gel Process, American Chemical Society, 1990, 33-72.

Joffe, et al, "Studies in silico-organic compounds VIII. the preparation and properties of polyethers from trichlorosilane, continued," Journal of Organic Chemistry, ACS, US, 1949, 421-428.

Larson, Gerald L., et al., "Preparation of alkyl(amino)dialkoxysilanes", Database CA [Online], Chemical Abstracts Service, Columbus, Ohio, US, retrieved from STN, Database accession No. 2000:623766.

Fushimi, Masaki, "Olefin polymerization catalysts and manufacture of polyolefins", Database CA [Online], Chemical Abstracts Service, Columbus, Ohio, US, retrieved from STN, Database accession No. 1995:693570.

Stewart, Constantine A., et al., "Substituted amino silane compounds and catalyst for the polymerization of.alpha-olefins containing them", Database CA [Online], Chemical Abstracts Service, Columbus, Ohio, US, retrieved from STN, Database accession No. 1999:425604.

Igai, Shigeru, et al., "High-activity and stereoregular catalysts for polymerization of alpha.-olefins", Database CA [Online], Chemical Abstracts Service, Columbus, Ohio, US, retrieved from STN, Database accession No. 1996:485735.

Larson, Gerald L. et al., "Preparation of alkyl(amino)dialkoxysilanes", Database CA [Online], Chemical Abstracts Service, Columbus, Ohio, US, retrieved from STN, Database accession No. 2000:493551.

* cited by examiner

ALKOXYAMINOSILANE COMPOUNDS AND APPLICATIONS THEREOF

CROSS-REFERENCE TO RELATED APPLICATIONS

This patent application is continuation-in-part application of U.S. Ser. No. 13/745,102, which claims the priority benefit of provisional patent application U.S. Ser. No. 61/591,318, entitled "Novel Alkoxyaminosilane Compounds and Applications Thereof" filed Jan. 27, 2012, which is incorporated herein by reference in its entirety.

BACKGROUND OF THE INVENTION

Described herein are volatile and thermally stable organoaminosilanes, more specifically, alkoxyaminosilanes, and their use for the deposition of stoichiometric or non-stoichiometric silicon-containing films such as, but not limited to silicon oxide, silicon nitride, silicon oxynitride, silicon carboxide, silicon oxycarbonitride films.

U.S. Pat. No. 4,491,669 discloses the preparation of pure mixed alkoxyaminosilanes corresponding to the general formula: $R_mSi(OR')_n(NR''R''')_p$ wherein: R is hydrogen, short chain alkyl or alkenyl or aryl; R" and R''' are separately either hydrogen, short chain alkyl or aryl, at least one being other than hydrogen; R' is short chain alkyl or aryl; and m, n and p are integers such that m+n+p=4 and n and p are at least one each. The obtained compounds are employed in end-capping of polysiloxanes having terminal silane groups.

U.S. Pat. No. 6,114,558 and WO 00/42049 disclose the preparation of alkyl(amino)dialkoxysilanes having the general formula $RSi(NR^1R^2)(OR^3)_2$, wherein R is a straight or branched chain alkyl of 1 to 20 carbon atoms, an arylalkyl or aryl radical, $R^1$ and $R^2$ arealkyl radicals of 1 to 6 carbon atoms and one of them can be hydrogen, and $R^3$ is an alkyl radical of 1-6 carbon atoms with methyl being preferred. The alkyl(amino)dialkoxysilanes are prepared by anhydrously reacting stoichiometric amounts of an alkoxysilane and an alkylaminomagnesium chloride in a reverse addition process. The alkylamino magnesium chloride is preferably prepared in situ by the reaction of a Grignard reagent (RMX) and an alkylamine in a suitable aprotic solvent, such as tetrahydrofuran (THF). The reaction can be conducted in a temperature range of from 25°-75° C., without a catalyst, and the aprotic solvent is recovered for re-use in the process. Thus, reaction of isopropylmagnesium chloride with tert-butylamine in THF followed by treatment with methyltrimethoxysilane gave 82% methyl(tert-butylamino)dimethoxysilane.

U.S. Pat. No. 7,524,735B1, U.S. Pat. No. 7,582,555B1, U.S. Pat. No. 7,888,233B1 and U.S. Pat. No. 7,915,139B1 disclose methods related to filling gaps on substrates with a solid dielectric material by forming a flowable film in the gap. The flowable film provides a consistent, void-free gap fill. The film is then converted to a solid dielectric material. In this manner gaps on the substrate are filled with a solid dielectric material. According to various embodiments, the methods involve reacting a dielectric precursor with an oxidant to form the dielectric material. In certain embodiments, the dielectric precursor condenses and subsequently reacts with the oxidant to form dielectric material. In certain embodiments, vapor phase reactants react to form a condensed flowable film.

U.S. Pat. No. 7,943,531 B2 discloses a method of depositing a silicon oxide layer over a substrate in a deposition chamber. A first silicon-containing precursor, a second silicon-containing precursor and a $NH_3$ plasma are reacted to form a silicon oxide layer. The first silicon-containing precursor includes at least one of Si—H bond and Si—Si bond. The second silicon-containing precursor includes at least one Si—N bond.

U.S. Pat. No. 7,425,350 B2 discloses a method for making a Si-containing material which comprises transporting a pyrolyzed Si-precursor to a substrate and polymerizing the pyrolyzed Si-precursor on the substrate to form a Si-containing film. Polymerization of the pyrolyzed Si-precursor may be carried out in the presence of a porogen to thereby form a porogen-containing Si-containing film. The porogen may be removed from the porogen-containing, Si-containing film to thereby form a porous Si-containing film. Preferred porous Si-containing films have low dielectric constants and thus are suitable for various low-k applications such as in microelectronics and microelectromechanic systems.

U.S. Pat. No. 4,345,088A discloses compounds having the formula $X(R)_2NSiHOR$ where X is OR or $N(R)_2$ and wherein R is an alkyl of from one to eight carbon atoms. These compounds are prepared by treating tris(dialkylamino)hydridosilanes with alkanols.

U.S. Pat. No. 7,888,273B discloses methods of lining and/or filling gaps on a substrate by creating flowable silicon oxide-containing films are provided. The methods involve introducing vapor-phase silicon-containing precursor and oxidant reactants into a reaction chamber containing the substrate under conditions such that a condensed flowable film is formed on the substrate. The flowable film at least partially fills gaps on the substrates and is then converted into a silicon oxide film. In certain embodiments the methods involve using a catalyst e.g. a nucleophile or onium catalyst in the formation of the film. The catalyst may be incorporated into one of the reactants and/or introduced as a separate reactant. Also provided are methods of converting the flowable film to a solid dielectric film. The methods of this invention may be used to line or fill high aspect ratio gaps including gaps having aspect ratios ranging from 3:1 to 10:1.

U.S. Pat. No. 7,629,227B discloses methods of lining and/or filling gaps on a substrate by creating flowable silicon oxide-containing films. The methods involve introducing vapor-phase silicon-containing precursor and oxidant reactants into a reaction chamber containing the substrate under conditions such that a condensed flowable film is formed on the substrate. The flowable film at least partially fills gaps on the substrates and is then converted into a silicon oxide film. In certain embodiments the methods involve using a catalyst e.g. a nucleophile or onium catalyst in the formation of the film. The catalyst may be incorporated into one of the reactants and/or introduced as a separate reactant. Also provided are methods of converting the flowable film to a solid dielectric film. The methods of this invention may be used to line or fill high aspect ratio gaps including gaps having aspect ratios ranging from 3:1 to 10:1.

WO 06129773 A1 disclosed a catalyst for polymerization of olefins formed from (A) a solid catalyst component containing magnesium titanium halogen and an electron donor compound (B) an organoaluminum compound shown by the formula R6pAlQ3-p and (C) an aminosilane compound shown by the formula $R^3{}_nSi(NR^4R^5)_{4-n}$; and a process for producing a catalyst for polymerization of olefins in the presence of the catalyst are provided. A novel aminosilane compound a catalyst component for polymerization of olefins having a high catalytic activity capable of producing polymers with high stereoregularity in a high yield and exhibiting an excellent hydrogen response a catalyst and a process for producing olefin polymers using the catalyst are provided.

Thus, there is a need in the art to provide precursors that can be used to deposit films comprising silicon that provide one or more of the following advantages: low processing temperatures (e.g., 300° C. or below); relatively good deposition rate; compositional uniformity; stability, and/or high purity.

BRIEF SUMMARY OF THE INVENTION

Described herein are alkoxyaminosilane precursors and methods using same for forming stoichiometric or non-stoichiometric films comprising silicon, such as, but not limited to, silicon oxide, carbon doped silicon oxide, silicon nitride, silicon oxynitride, silicon carbide, silicon carbonitride, and combinations thereof onto at least a portion of a substrate. Also disclosed herein are the methods to form dielectric films or coatings on an object to be processed, such as, for example, a semiconductor wafer.

Alkoxyaminosilane compounds and methods to prepare stoichiometric or non-stoichiometric silicon containing films employ a family of alkoxyaminosilane precursors having a general formula (I):

$(R^1R^2)NSiR^3OR^4OR^5$          Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. Examples of this embodiments include, but are not limited to, dimethoxy(cis-2,6-dimethylpiperidino)silane, diethoxy(cis-2,6-dimethylpiperidino)silane, dimethoxy(cis-2,6-dimethylpiperidino)methylsilane, diethoxy(cis-2,6-dimethylpiperidino) methylsilane, dimethoxy(trans-2,6-dimethylpiperidino) silane, diethoxy(trans-2,6-dimethylpiperidino)silane, dimethoxy(trans-2,6-dimethylpiperidino)methylsilane, and diethoxy(trans-2,6-dimethylpiperidino)methylsilane. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. Examples of the later embodiments include, but are not limited to, diethoxy(tert-butylamino)silane and dimethoxy(tert-butylamino)silane.

In another aspect, there is provided a method for forming a silicon-containing film on at least one surface of a substrate comprising:
providing the at least one surface of the substrate in a reaction chamber; and
forming the silicon-containing film on the at least one surface by a deposition process chosen from a chemical vapor deposition process and an atomic layer deposition process using at least one precursor comprising an alkoxyaminosilane having a general formula (I):

$(R^1R^2)NSiR^3OR^4OR^5$          Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. In one particular embodiment of Formula I, $R^1$ and $R^2$ can be linked together to form a ring. In another embodiment of Formula I, $R^1$ and $R^2$ are not linked together to form a ring.

In another aspect, there is provided a method of forming a silicon oxide or carbon doped silicon oxide film via an atomic layer deposition process or cyclic chemical vapor deposition process, the method comprising the steps of:
a. providing a substrate in a reactor;
b. introducing into the reactor at least one precursor comprising an alkoxyaminosilane having a general formula (I):

$(R^1R^2)NSiR^3OR^4OR^5$          Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. In one particular embodiment of Formula I, $R^1$ and $R^2$ can be linked together to form a ring. In another embodiment of Formula I, $R^1$ and $R^2$ are not linked together to form a ring;
c. purging the reactor with a purge gas;
d. introducing an oxygen source into the reactor;
e. purging the reactor with a purge gas; and
repeating the steps b through e until a desired thickness of the film is obtained.

In a further aspect, there is provided a method of forming a silicon oxide or carbon doped silicon oxide film onto at least a surface of a substrate using a CVD process comprising:
a. providing a substrate in a reactor;
b. introducing into the reactor at least one precursor comprising an alkoxyaminosilane having a general formula (I):

$(R^1R^2)NSiR^3OR^4OR^5$          Formula (I)

wherein $R^1$ is independently selected from a linear or branched $C_1$ to $C_{10}$ alkyl group; a $C_2$ to $C_{12}$ alkenyl group;

a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. In one particular embodiment of Formula I, $R^1$ and $R^2$ can be linked together to form a ring. In another embodiment of Formula I, $R^1$ and $R^2$ are not linked together to form a ring; and c. providing an oxygen source to deposit the silicon oxide or carbon doped silicon oxide film onto the at least one surface.

In another aspect, there is provided a method of forming a silicon nitride or silicon oxynitride or silicon carboxynitride film via an atomic layer deposition process or cyclic chemical vapor deposition process, the method comprising the steps of:

a. providing a substrate in a reactor;

b. introducing into the reactor an at least one precursor comprising an alkoxyaminosilane having a general formula (I):

  Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. In one particular embodiment of Formula I, $R^1$ and $R^2$ can be linked together to form a ring. In another embodiment of Formula I, $R^1$ and $R^2$ are not linked together to form a ring;

c. purging the reactor with a purge gas;

d. introducing a nitrogen-containing source into the reactor;

e. purging the reactor with a purge gas; and repeating the steps b through e until a desired thickness of the silicon nitride or silicon oxynitride or silicon carboxynitride film is obtained.

In a further aspect, there is provided a method of forming a silicon nitride or silicon oxynitride film onto at least a surface of a substrate using a CVD process comprising:

a. providing a substrate in a reactor;

b. introducing into the reactor at least one precursor comprising an alkoxyaminosilane having a general formula (I):

  Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. In one particular embodiment of Formula I, $R^1$ and $R^2$ can be linked together to form a ring. In another embodiment of Formula I, $R^1$ and $R^2$ are not linked together to form a ring; and c. providing a nitrogen-containing source wherein the at least one organoaminosilane precursors and the nitrogen-containing source react to deposit the film comprising both silicon and nitrogen onto the at least one surface.

In another aspect, a vessel for depositing a dielectric film comprising one or more alkoxyaminosilane precursor having Formula I or A is described herein. In one particular embodiment, the vessel comprises at least one pressurizable vessel (preferably of stainless steel) fitted with the proper valves and fittings to allow the delivery of one or more precursors to the reactor for a CVD or an ALD process.

In yet another aspect, there is provided a composition for the deposition of a dielectric film comprising: at least one precursor comprising an alkoxyaminosilane having a general formula (I):

  Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring. Examples of this embodiments include, but are not limited to, dimethoxy(cis-2,6-dimethylpiperidino)silane, diethoxy(cis-2,6-dimethylpiperidino)silane, dimethoxy(cis-2,6-dimethylpiperidino)methylsilane, and diethoxy(cis-2,6-dimethylpiperidino)methylsilane. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked together. In certain embodiments of Formula I, $R^2$ and $R^3$ are both hydrogen. Examples of the later embodiments include, but are not limited to, diethoxy(tert-butylamino)silane and dimethoxy(tert-butylamino)silane.

DETAILED DESCRIPTION OF THE INVENTION

Alkoxyaminosilanes are used as precursors to deposit stoichiometric and non-stoichiometric silicon containing films such as, but not limited to, silicon oxide, silicon oxycarbide, silicon nitride, silicon oxynitride and silicon oxycarbonitride using a variety of deposition processes. The alkoxyaminosilanes described herein include aryloxyaminosilanes, alkoxyaminosilanes, and combinations thereof. The deposition processes include, but are not limited to, chemical vapor deposition, plasma enhanced chemical vapor deposition, cyclic chemical vapor deposition, flowable chemical vapor deposition (FCVD), atomic layer deposition, plasma enhanced atomic layer deposition. The alkoxyaminosilane precursors are typically high purity volatile liquid precursors that are vaporized and delivered to a deposition chamber or reactor as a gas to deposit a silicon containing film via various deposition techniques including, but not limited to, chemical vapor deposition (CVD), cyclic chemical vapor deposition (CCVD), flowable chemical vapor deposition (FCVD), atomic layer deposition (ALD) for semiconductor devices. In other embodiments, the alkoxyaminosilane precursors can be used in a liquid-based deposition or film formation method such as, but not limited to, spin-on, dip coat, aerosol, ink jet, screen printing or spray application. The selection of precursor materials for deposition depends upon the desired resultant dielectric material or film. For example, a precursor material may be chosen for its content of chemical elements, its stoichiometric ratios of the chemical elements, and/or the resultant dielectric film or coating that are formed under aforementioned deposition processes. The precursor material may also be chosen for one or more of the following characteristics: cost, non-toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of the liquid phase precursor to the deposition chamber or reactor.

It is believed that the alkoxyaminosilane precursors described herein may provide better reactivity towards substrate surface during chemical vapor deposition or atomic layer deposition because the precursors have Si—N, Si—O, optionally Si—H, optionally Si—NH functionalities, which allow them to chemically react on substrate surfaces during a vapor deposition process. It is believed that the alkoxyaminosilanes precursors described herein may provide better reactivity towards substrate surface during chemical vapor deposition, particularly cyclic CVD deposition, or atomic layer deposition to form Si—N—Si linkage or Si—O—Si linkage due to their chemical characteristics such as optionally Si—H, Si—OR, and optionally Si—NHR bonds. In addition to the foregoing advantages, in certain embodiments such as for depositing a silicon oxide or silicon nitride film using a cyclic CVD, an ALD, or PEALD deposition method, the alkoxyaminosilane precursor described herein may be able to deposit high density materials at relatively low deposition temperatures, e.g., at 500° C. or less, at 400° C. or less, or at 300° C. or less. In other embodiments, the precursors described herein can be used, for example, in higher temperature deposition at temperatures ranging from about 500° C. to about 800° C.

In one embodiment, described herein are deposition processes employing an alkoxyaminosilane having a general formula (I):

  Formula (I)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group.

In certain embodiments, $R^1$ and $R^2$ in Formula I can be linked together to form a ring. In other embodiments, $R^1$ and $R^2$ in Formula I are not linked together to form a ring. In certain embodiments, $R^4$ and $R^5$ in Formula I can be linked together. In the other embodiments, $R^4$ and $R^5$ in Formula I are not linked. In the foregoing embodiments, the ring can be a hydrocarbon cyclic or an aromatic ring.

Also described herein are alkoxyaminosilanes compounds derived from the general formula (I) wherein $R^2$ and $R^3$ are both hydrogen which is shown as formula A:

 (A)

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments of Formula A, $R^4$ and $R^5$ in Formula I can be linked together. In the other embodiments, $R^4$ and $R^5$ in Formula I are not linked together. The key features of those alkoxyaminosilanes compounds are that they all have Si—N, Si—O, Si—H as well as Si—NH functionalities which allow them to chemically react on substrate surfaces during a vapor deposition process.

In one particular embodiment of Formula A, $R^1$ is selected from tert-butyl or tert-pentyl while $R^4$ and $R^5$ are independently selected from $C_1$ to $C_5$ alkyl groups such as ethyl, n-propyl, iso-propyl, n-butyl, sec-butyl, iso-butyl, tert-butyl. In another embodiment of Formula A, $R^1$ is selected from $C_1$ to $C_5$ alkyl groups such as ethyl, n-propyl, iso-propyl, n-butyl, sec-butyl, iso-butyl, tert-butyl while $R^4$ and $R^5$ are independently selected from branched $C_3$ to $C_5$ alkyl groups such as iso-propyl, sec-butyl, iso-butyl, tert-butyl, and tert-pentyl. Examples of embodiments of Formula A include, but are not limited to, diethoxy(tert-butylamino)silane, dimethoxy(tert-butylamino)silane, diethoxy(tert-pentylamino)silane and dimethoxy(tert-pentylamino)silane.

In another particular embodiment derived from the general formula (I) wherein $R^1$ and $R^2$ are linked together form a ring, and $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In this embodiments, $R^4$ and $R^5$ in Formula I can be linked together or not be linked together. Examples of such embodiment include, but are not limited to dimethoxy(cis-2,6-dimethylpiperidino)silane, diethoxy(cis-2,6-dimethylpiperidino)silane, dimethoxy(cis-2,6-dimethylpiperidino)methylsilane, and diethoxy(cis-2,6-dimethylpiperidino)methylsilane.

The following Schemes 1 and 2 provide examples of reaction schemes or synthesis routes which may be used to make the halogenated organoaminosilanes having formula I wherein $R^5$ is same as $R^4$ as described herein. Reaction schemes 1 and 2 can be conducted with (e.g., in the presence of) organic solvents. In embodiments wherein an organic solvent is used, examples of suitable organic solvents include, but are not limited to, hydrocarbon such as hexanes, octane, toluene, and ethers such as diethylether, and tetrahydrofuran (THF). In these or other embodiments, the reaction temperature is in the range of from about −70° C. to the boiling point of the solvent employed if a solvent is involved. The resulting alkoxyaminosilanes can be purified via vacuum distillation after removing all by-products as well as solvent(s).

Scheme 1

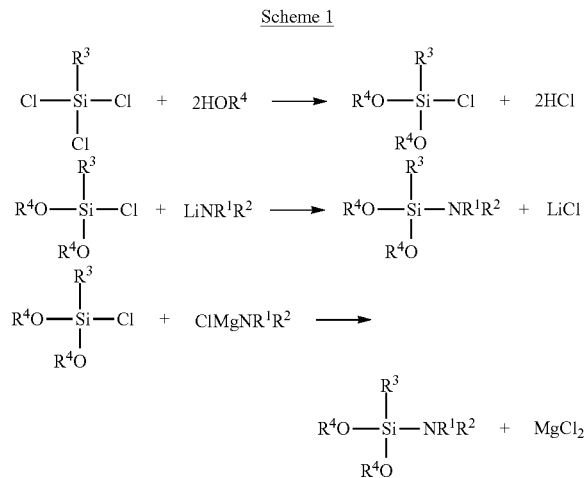

Scheme 2

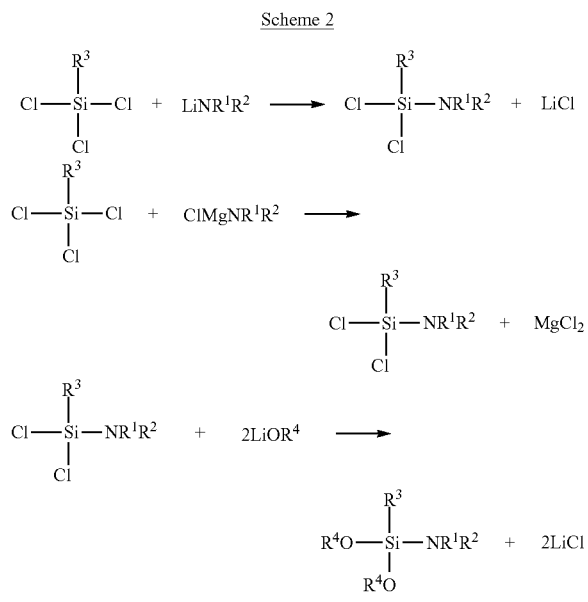

In Formulas I and A and throughout the description, the term "alkyl" denotes a linear, or branched functional group having from 1 to 10 or 1 to 4 carbon atoms. Exemplary alkyl groups include, but are not limited to, methyl, ethyl, n-propyl, isopropyl, n-butyl, isobutyl, sec-butyl, tert-butyl, n-pentyl, iso-pentyl, tert-pentyl, hexyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In Formulas I and A and throughout the description, the term "cyclic alkyl" denotes a cyclic functional group having from 3 to 12 or from 4 to 10 carbon atoms. Exemplary cyclic alkyl groups include, but are not limited to, cyclobutyl, cyclopentyl, cyclohexyl, and cyclooctyl groups.

In Formulas I and A and throughout the description, the term "aryl" denotes an aromatic cyclic functional group having from 6 to 12 carbon atoms. Exemplary aryl groups include, but are not limited to, phenyl, benzyl, chlorobenzyl, tolyl, and o-xylyl.

In Formulas I and A and throughout the description, the term "alkenyl group" denotes a group which has one or more carbon-carbon double bonds and has from 2 to 12 or from 2 to 6 carbon atoms. Exemplary alkenyl groups include, but are not limited to, vinyl or allyl groups In Formulas I and A and throughout the description, the term "alkynyl group" denotes a group which has one or more carbon-carbon triple bonds and has from 2 to 12 or from 2 to 6 carbon atoms.

In Formulas I and A and throughout the description, the term "alkoxy" denotes an alkyl group which has is linked to an oxygen atom (e.g., R—O) and may have from 1 to 12, or from 1 to 6 carbon atoms. Exemplary alkoxy groups include, but are not limited to, methoxy (—OCH$_3$), ethoxy(—OCH$_2$CH$_3$), n-propoxy (—OCH$_2$CH$_2$CH$_3$), and iso-propoxy (—OCHMe$_2$).

In certain embodiments, one or more of the alkyl group, alkenyl group, alkynyl group, alkoxy group, and/or aryl group in Formulas I and A may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In one particular embodiment, the alkyl group in Formula I or A may comprise oxygen or nitrogen. In other embodiments, one or more of the alkyl group, alkenyl group, alkynyl group, alkoxy group, and/or aryl in Formula I may be unsubstituted.

Examples of the alkoxyaminosilane of Formula I or A described herein include, but are not limited to, di-ethoxy(tert-butylamino)silane, diethoxy(tert-pentylamino)silane, diethoxy(iso-propoxyamino)silane, diethoxy(tert-butylamino)silane, diethoxy(tert-pentylamino)silane, diethoxy(iso-propoxyamino)silane, di-tert-butoxy(methylamino)silane, di-tert-butoxy(ethylamino)silane, ditert-butoxy(iso-propylamino)silane, di-tert-butoxy(n-butylamino)silane, di-tert-butoxy(sec-butylamino)silane, di-tert-butoxy(iso-butylamino)silane, di-tert-butoxy(tert-butylamino)silane, di-tert-pentoxy(methylamino)silane, di-tert-pentoxy(ethylamino)silane, di-tert-pentoxy(iso-propylamino)silane, di-tert-pentoxy(n-butylamino)silane, di-tert-pentoxy(sec-butylamino)silane, di-tert-pentoxy(iso-butylamino)silane, di-tert-pentoxy(tert-butylamino)silane, dimethoxy(phenylmethylamino)silane, diethoxy(phenylmethylamino)silane, dimethoxy(phenylmethylamino)methylsilane, and diethoxy(phenylmethylamino)methylsilane, dimethoxy(cis-2,6-dimethylpiperidino)silane, diethoxy(cis-2,6-dimethylpiperidino)silane, dimethoxy(cis-2,6-dimethylpiperidino)methylsilane, and diethoxy(cis-2,6-dimethylpiperidino)methylsilane.

Examples of the alkoxyaminosilane of Formula I or A wherein $R^3$ is methyl, include but are not limited to, diethoxy(tert-butylamino)methylsilane, diethoxy(tert-pentylamino)methylsilane, diethoxy(iso-propoxyamino)methylsilane, diethoxy(tert-butylamino)methylsilane, diethoxy(tert-pentylamino)methylsilane, diethoxy(iso-propoxyamino)methylsilane, di-tert-butoxy(methylamino)methylsilane, di-tert-butoxy(ethylamino)methylsilane, ditert-butoxy(iso-propylamino)methylsilane, di-tert-butoxy(n-butylamino)methylsilane, di-tert-butoxy(sec-butylamino)methylsilane, di-tert-butoxy(iso-butylamino)methylsilane, di-tert-butoxy(tert-butylamino)methylsilane, di-tert-pentoxy(methylamino)methylsilane, di-tert-pentoxy(ethylamino)methylsilane, di-tert-pentoxy(iso-propylamino)methylsilane, di-tert-pentoxy(n-butylamino) methylsilane, di-tert-pentoxy(sec-butylamino)methylsilane, di-tert-pentoxy(iso-butylamino)methylsilane, di-tert-pentoxy(tert-butylamino)methylsilane, dimethoxy(phenylmethylamino)methylsilane, and diethoxy (phenylmethylamino)methylsilane.

In certain embodiments of the invention described herein, the alkoxyaminosilane precursor having the above formula I or A can be combined with one or more silicon-containing precursor selected from the group consisting of dialkylaminosilanes, alkoxysilanes, dialkylaminoalkylsilanes, and alkoxyalkylsilanes to provide a composition for depositing a dielectric film. In these embodiments, the composition comprises an alkoxyaminosilane having formula I or A and a silicon-containing precursor. Examples of silicon-containing precursors for these compositions include, but not limited to, bis(tert-butylamino)silane (BTBAS), tris(dimethylamino)silane (TRDMAS), tetraethoxysilane (TEOS), triethoxysilane (TES), di-tert-butoxysilane (DTBOS), di-tert-pentoxysilane (DTPOS), methyltriethoxysilane (MTES), tetramethoxysilane (TMOS), trimethoxysilane (TMOS), methyltrimethoxysilane (MTMOS), di-tert-butoxymethylsilane, di-tert-butoxyethylsilane, di-tert-pentoxymethylsilane, and di-tert-pentoxyethylsilane.

Examples of the compositions comprising silicon-containing precursor and an alkoxyaminosilane of Formula I or A include, but are not limited to, tetraethoxysilane (TEOS) and di-ethoxy(tert-butylamino)silane, tetraethoxysilane (TEOS) and diethoxy(tert-pentylamino)silane, tetraethoxysilane (TEOS) and diethoxy(iso-propoxyamino)silane, triethoxysilane (TES) and diethoxy(tert-butylamino)silane, triethoxysilane (TES) and diethoxy(tert-pentylamino)silane, triethoxysilane (TES) and diethoxy(iso-propoxyamino)silane, di-tert-butoxysilane (DTBOS) and di-tert-butoxy(methylamino)silane, di-tert-butoxysilane (DTBOS) and-di-tert-butoxy(ethylamino)silane, di-tert-butoxysilane (DTBOS) and ditert-butoxy(iso-propylamino)silane, di-tert-butoxysilane (DTBOS) and di-tert-butoxy(n-butylamino)silane, di-tert-butoxysilane (DTBOS) and di-tert-butoxy(sec-butylamino)silane, di-tert-butoxysilane (DTBOS) and di-tert-butoxy(iso-butylamino)silane, di-tert-butoxysilane (DTBOS) and di-tert-butoxy(tert-butylamino)silane, di-tert-pentoxysilane (DTPOS) and di-tert-pentoxy(methylamino)silane, di-tert-pentoxysilane (DTPOS) and di-tert-pentoxy(ethylamino)silane, di-tert-pentoxysilane (DTPOS) and di-tert-pentoxy(iso-propylamino)silane, di-tert-pentoxysilane (DTPOS) and di-tert-pentoxy(n-butylamino)silane, di-tert-pentoxysilane (DTPOS) and di-tert-pentoxy(sec-butylamino)silane, di-tert-pentoxysilane (DTPOS) and di-tert-pentoxy(iso-butylamino)silane, di-tert-pentoxysilane (DTPOS) and di-tert-pentoxy(tert-butylamino)silane. In one particular embodiment, the composition is used to deposit a silicon oxide film by flowable chemical vapor deposition wherein the alkoxyaminosilane having formula I or A acts as a catalyst. In this or other embodiments, the silicon-containing precursor is selected to be compatible with the alkoxyaminosilane by having, for example, the same alkoxy substituent.

The deposition method used to form the silicon-containing dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, deposition from supercritical fluids, and low energy CVD (LECVD), and flowable chemical vapor deposition.

In one particular embodiment, such as for depositing a silicon oxide using typical FCVD processes, the alkoxyaminosilane precursor described herein may be used in combination with other silicon-containing precursors such as those compositions described herein as a catalyst due to release of organoamine as an in situ catalyst at relatively low deposition temperatures, e.g., at 100° C. or less, 50° C. or less, 20° C. or less, even 0° C. or lower.

As used herein, the term "chemical vapor deposition processes" refers to any process wherein a substrate is exposed to one or more volatile precursors, which react and/or decompose on the substrate surface to produce the desired deposition.

As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator.

In one embodiment, the dielectric film is deposited using an ALD process. In another embodiment, the dielectric film is deposited using a CCVD process. In a further embodiment, the dielectric film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the dielectric film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

Depending upon the deposition method, in certain embodiments, alkoxyaminosilane precursors with formula I or A, other silicon-containing precursors may be introduced into the reactor at a predetermined molar volume, or from about 0.1 to about 1000 micromoles. In this or other embodiments, the alkoxyaminosilane precursor may be introduced into the reactor for a predetermined time period. In certain embodiments, the time period ranges from about 0.001 to about 500 seconds.

In certain embodiments, the dielectric films deposited using the methods described herein are formed in the presence of oxygen using an oxygen source, reagent or precursor comprising oxygen.

An oxygen source may be introduced into the reactor in the form of at least one oxygen source and/or may be present incidentally in the other precursors used in the deposition process.

Suitable oxygen source gases may include, for example, water ($H_2O$) (e.g., deionized water, purifier water, and/or distilled water, a mixture containing water and other organic liquid), oxygen ($O_2$), oxygen plasma, ozone ($O_3$), NO, $NO_2$, water plasma, carbon monoxide (CO), carbon dioxide ($CO_2$) and combinations thereof. The organic liquid in the mixture can be selected from hydrocarbon, aromatic hydrocarbon, ether, amine, ketone, ester, organic acid, and organic amide.

In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds.

In one particular embodiment, the oxygen source comprises water having a temperature of 10° C. or greater.

In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds.

In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited dielectric film.

In certain embodiments, oxygen source is continuously flowing into the reactor while precursor pulse and plasma are introduced in sequence. The precursor pulse can have a pulse duration greater than 0.01 seconds while the plasma duration can range between 0.01 seconds to 100 seconds.

In certain embodiments, the dielectric films comprise silicon and nitrogen. In these embodiments, the dielectric films deposited using the methods described herein are formed in the presence of nitrogen-containing source. An nitrogen-containing source may be introduced into the reactor in the form of at least one nitrogen source and/or may be present incidentally in the other precursors used in the deposition process.

Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof.

In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm.

The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors.

Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting dielectric film.

Energy is applied to the at least one of the precursor, nitrogen-containing source, reducing agent, other precursors or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof.

In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The alkoxyaminosilane precursors and/or other silicon-containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting dielectric film.

In another embodiment of the method disclosed herein, the films containing both silicon and nitrogen are formed using a ALD deposition method that comprises the steps of:
   providing a substrate in an ALD reactor;
   introducing into the ALD reactor at least one precursor comprising an alkoxyaminosilane having a general formula (I):

$$(R^1R^2)NSiR^3OR^4OR^5 \quad \text{Formula (I)}$$

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; wherein $R^2$ and $R^3$ are linked to form a ring or $R^2$ and $R^3$ are not linked to form a ring and wherein $R^4$ and $R^5$ are linked to form a ring or $R^2$ and $R^3$ are not linked to form a ring;
   chemisorbing the at least one alkoxyaminosilane precursor onto a substrate;
   purging away the unreacted at least one organoaminosilane precursor using a purge gas;
   providing a nitrogen-containing source to the organoaminosilane precursor onto the heated substrate to react with the sorbed at least one organoaminosilane precursor; and
   optionally purging away any unreacted nitrogen-containing source.

In another embodiment of the method disclosed herein, the dielectric films is formed using a ALD deposition method that comprises the steps of:
   providing a substrate in a reactor;
   introducing into the reactor an at least one precursor comprising an alkoxyaminosilane having a general formula (I):

$$(R^1R^2)NSiR^3OR^4OR^5 \quad \text{Formula (I)}$$

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ are each independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group. In certain embodiments, $R^1$ and $R^2$ in Formula I can be linked together to form a ring
   chemisorbing the at least one organoaminosilane precursor onto a substrate;
   purging away the unreacted at least one organoaminosilane precursor using a purge gas;
   providing an oxygen source to the organoaminosilane precursor onto the heated substrate to react with the sorbed at least one organoaminosilane precursor; and
   optionally purging away any unreacted oxygen source.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, reducing agents, or other reagents can be alternately introduced into the reactor chamber.

In a further embodiment of the method described herein, the dielectric film is deposited using a thermal CVD process. In this embodiment, the method comprises:
   placing one or more substrates into a reactor which is heated to a temperature ranging from ambient temperature to about 700° C. and maintained at a pressure of 1 Torr or less;
   introducing at least one precursor comprising an alkoxyaminosilane having a general formula (I):

$$(R^1R^2)NSiR^3OR^4OR^5 \quad \text{Formula (I)}$$

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ areeach independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; and
   providing an oxygen source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, oxygen sources, reducing agents, and/or other reagents can be alternately introduced into the reactor chamber.

In a further embodiment of the method described herein, the dielectric film is deposited using a thermal CVD process. In this embodiment, the method comprises:
   placing one or more substrates into a reactor which is heated to a temperature ranging from ambient temperature to about 700° C. and maintained at a pressure of 1 Torr or less;
   introducing at least one precursor comprising an alkoxyaminosilane having a general formula (I):

$$(R^1R^2)NSiR^3OR^4OR^5 \quad \text{Formula (I)}$$

wherein $R^1$ is independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; $R^2$ and $R^3$ areeach independently selected from hydrogen; a linear or branched $C_1$ to $C_{10}$ alkyl group; a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^4$ and $R^5$ are each independently selected from a linear or branched $C_1$ to $C_{10}$ alkyl group; a $C_2$ to $C_{12}$ alkenyl group; a $C_2$ to $C_{12}$ alkynyl group; a $C_4$ to $C_{10}$ cyclic alkyl group; and a $C_6$ to $C_{10}$ aryl group; and providing a nitrogen-containing source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

As previously mentioned, the process described herein can be used to deposit a film using more than one precursor such as the alkoxyaminosilane having Formula I or A described herein with an additional precursor such as another silicon-containing precursor such as those described herein. In these embodiments, the one or more precursors are described as a first precursor, a second precursor, a third precursor, etc. depending upon the number of different precursors used. The process can be used, for example, in a cyclic chemical vapor deposition or an atomic layer deposition. In these or other embodiments, the precursors can be introduced in a variety of ways (e.g., a) introduce first precursor; b) purge; c) introduce second precursor; d) purge; e) introduce third precursor; f) purge, etc., or, alternatively, a) introduce first precursor; b) purge; c) introduce second precursor; d) purge; e) introduce second precursor; etc.) In one particular embodiment, there is provided a process to deposit silicon oxide film or a silicon, carbon, and oxide film comprising the following steps:

a). Contacting vapors generated from a first precursor with a heated substrate to chemically sorb the first precursor on the heated substrate;

b). Purging away any unsorbed precursors;

c). Introducing an oxygen source on the heated substrate to react with the sorbed first precursor;

d). Purging away any unreacted oxygen source;

e). Contacting vapors generated from a second precursor which is different from the first precursor with a heated substrate to chemically sorb the second precursor on the heated substrate;

f). Purging away any unsorbed precursors;

g). Introducing an oxygen source on the heated substrate to react with the sorbed first and second precursors; and h) Purging away any unreacted oxygen source wherein steps a). through h). are repeated until a desired thickness has been reached.

In a yet another embodiment of the process described herein, there is provided a method of depositing a silicon nitride or silicon carbonitride or silicon oxycarbonitride film comprising the following steps:

a). Contacting vapors generated from a first precursor with a heated substrate to chemically sorb the first precursors on the heated substrate;

b). Purging away any unsorbed first precursors;

c). Introducing a nitrogen source on the heated substrate to react with the sorbed first precursor;

d). Purging away any unreacted nitrogen source;

e). Contacting vapors generated from a second precursor which is different from the first with a heated substrate to chemically sorb the second precursor on the heated substrate;

f). Purging away any unsorbed second precursors;

g). Introducing a nitrogen source on the heated substrate to react with the sorbed second precursor; and h). Purging away any unreacted nitrogen source wherein steps a) through h) are repeated until a desired thickness has been reached.

In a further embodiment, described herein is a process is deposit silicon-containing films employing cyclic chemical vapor deposition (CCVD) or atomic layer deposition (ALD) techniques such as, but not limited to, plasma enhanced ALD (PEALD) or plasma enhanced CCVD (PECCVD) process. In these embodiments, the deposition temperature may be relatively high, or from about 500 to 800° C., to control the specifications of film properties required in certain semiconductor applications. In one particular embodiment, the process comprises the following steps: contacting vapors generated from an alkoxyaminosilane having Formula I or A with a heated substrate to chemically sorb the precursors on the heated substrate; purging away any unsorbed precursors; introducing a reducing agent to reduce the sorbed precursors; and purging away any unreacted reducing agent.

In another embodiment, a vessel for depositing a dielectric film comprising one or more alkoxyaminosilane precursor having formula I or A is described herein.

In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the organoaminosilane precursor is provided in a pressurizable vessel comprised of stainless steel and the purity of the precursor is 98% by weight or greater or 99.5% or greater which is suitable for the majority of semiconductor applications.

In certain embodiments, such vessels can also have means for mixing the precursors with one or more additional precursor if desired. In these or other embodiments, the contents of the vessel(s) can be premixed with an additional precursor. Alternatively, the organoaminosilane precursor and/or other precursor can be maintained in separate vessels or in a single vessel having separation means for maintaining the organoaminosilane precursor and other precursor separate during storage.

In one embodiment of the method described herein, a cyclic deposition process such as CCVD, ALD, or PEALD may be employed, wherein at least one silicon-containing precursor selected from an alkoxyaminosilane precursor having formula I or A and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nano-electromechanical systems, thin film transistor (TFT), and liquid crystal displays (LCD).

In the specification and claims, letters are used to identify claimed steps (e.g. (a), (b), and (c)). These letters are used to aid in referring to the method steps and are not intended to indicate the order in which claimed steps are performed, unless and only to the extent that such order is specifically recited in the claims.

WORKING EXAMPLES

Example 1

Synthesis of Diethoxy(tert-butylamino)silane

To a solution of 1.00 g (7.38 mmol) trichlorosilane in 5 mL of hexanes at room temperature was added a solution of 0.68 g (14.77 mmol) anhydrous ethanol in hexanes drop-wise. After addition, bubbling was witnessed and the reaction was allowed to agitate via a magnetic stir bar for one hour while purging under nitrogen. After one hour, a solution of 1.08 g (14.77 mmol) tert-butylamine in hexanes was added drop-wise and the reaction became a white slurry. After one hour of stirring, a sample was taken and ran GC/MS and showed evidence of the 176 amu fragmental peak (parent ion minus 15) of the desired product diethoxy(tert-butylamino)silane.

Example 2

Synthesis of Dimethoxy(tert-butylamino)silane

To a solution of 1.00 g (7.38 mmol) trichlorosilane in 5 mL of hexanes at room temperature was added a solution of 0.47 g (14.77 mmol) anhydrous methanol in hexanes drop-wise. After addition, bubbling was witnessed and the reaction was allowed to agitate via a magnetic stir bar for one hour while purging under nitrogen. After one hour, a solution of 1.08 g (14.77 mmol) tert-butylamine in hexanes was added drop-wise and the reaction became a white slurry. After one hour of stirring, a sample was taken and ran GC/MS and showed evidence of the 148 amu fragmental peak (parent ion minus 15 (one methyl)) of the desired product dimethoxy(tert-butylamino)silane.

Example 3

Synthesis of Diethoxy(iso-propylamino)silane

To a solution of 1.00 g (7.38 mmol) trichlorosilane in 5 mL of hexanes at room temperature was added a solution of 0.68 g (14.77 mmol) anhydrous ethanol in hexanes drop-wise. After addition, bubbling was witnessed and the reaction was allowed to agitate via a magnetic stir bar for one hour while purging under nitrogen. After one hour, a solution of 0.87 g (14.77 mmol) iso-propylamine in hexanes was added drop-wise and the reaction became a white slurry. After one hour of stirring, a sample was taken and ran GC/MS and showed evidence of the 162 amu fragmental peak (parent ion minus 15 (one methyl)) of the desired product diethoxy(iso-propylamino)silane.

Example 4

Synthesis of Dimethoxy(cis-2,6-dimethylpiperidino)silane

To a solution of 106.79 g (502.81 mmol) (cis-2,6-dimethylpiperidino)dichlorosilane in 300 mL of hexanes was added 38.18 g (1005.62 mmol) lithium methoxide prepared in situ via reacting methanol and n-butyllithium. The reaction was stirred with a magnetic stir bar for the extent of 16 hours after which it was filtered to yield 48.44 g of lithium chloride salt. GC-MS indicates the desired product with a parent ion of 203 amu (major fragmental peak at 188 amu). The filtrate was removed of solvent and the desired product was purified via vacuum distillation at 1.25 Torr while heating at 70° C. The yield was 61.1%.

Heating of the desired dimethoxy(cis-2,6-dimethylpiperidino)silane at 80° C. in a closed stainless steel tube for one week showed no degradation.

Example 5

Synthesis of Diethoxy(cis-2,6-dimethylpiperidino)silane

To a solution of 91.69 g (432.13 mmol) (cis-2,6-dimethylpiperidino)dichlorosilane in 300 mL of hexanes was added 44.94 g (864.27 mmol) lithium ethoxide prepared in situ via reacting ethanol and n-butyllithium. The reaction was stirred with a magnetic stir bar for the extent of 16 hours after which it was filtered yielding a white salt. The filtrate was removed of solvent by static distillation and GC-MS indicates desired product with a parent ion of 231 amu (major fragmental peak at 216 amu).

Heating of the desired diethoxy(cis-2,6-dimethylpiperidino)silane at 80° C. in a closed stainless steel tube for one week showed about 0.16% degradation.

Example 6

Synthesis of Dimethoxy(cis-2,6-dimethylpiperidino)methylsilane

To a solution of 1.00 g (7.11 mmol) dimethoxymethylchlorosilane in 3 mL of hexanes was added a solution of 1.61 g (14.22 mmol) cis-2,6-dimethylpiperidine in 2 mL of hexanes drop-wise. A white precipitate slowly evolved. After five days of agitation, GC-MS indicates the desired product, dimethoxymethyl(cis-2,6-dimethylpiperidino)silane, with a parent ion at 217 amu (major fragmental peak at 202 amu).

Example 7

Synthesis of Diethoxy(cis-2,6-dimethylpiperidino)ethylsilane

To a solution of 0.80 g (4.74 mmol) diethoxymethylchlorosilane in 3 mL of hexanes was added a solution of 1.10 g (9.48 mmol) cis-2,6-dimethylpiperidine in 2 mL of hexanes drop-wise. A white precipitate slowly evolved. After six days of agitation, GC-MS indicates desired product with a parent ion at 245 amu (major fractional peak at 230 amu)

Example 8

Atomic Layer Deposition of Silicon-containing Film Using Ozone Process

Atomic layers depositions of silicon-containing films were conducted using dimethoxy(cis-2,6-dimethylpiperidino)silane. The depositions were performed on a laboratory scale ALD processing tool at a 300° C. deposition temperature. All gases (e.g., purge and reactant gas or precursor and oxygen source) were preheated to 100° C. prior to entering the deposition zone. Gases and precursor flow rates were controlled with ALD valves with high speed actuation. The substrates used in the deposition were 12 inch length silicon strips having thermocouples attached on a sample holder to confirm the substrate temperature. Depositions were performed using ozone as the oxygen source gas and the process parameters of the depositions are provided in Table I using the following process steps:

Step 1. Contacting vapors of dimethoxy(cis-2,6-dimethylpiperidino)silane for 2 seconds Step 2. Purging away any unsorbed dimethoxy(cis-2,6-dimethylpiperidino)silane Step 3. Introducing ozone to react with the sorbed dimethoxy(cis-2,6-dimethylpiperidino)silane for 4 seconds Step 4. Purging away any unreacted ozone Steps 1 through 4 were repeated 350 times to achieve a desired thickness as shown in Table 1.

TABLE 1

Summary of Resulting Silicon-containing Films dimethoxy(cis-2,6-dimethylpiperidino)silane using ozone process at 300° C.

| No. of Cycles | Thickness (Å) | Dep Rate (Å/cycle) | Ref. index | Non-uniformity (%) |
|---|---|---|---|---|
| 350 | 478 | 1.4 | 1.46 | 2.7 |

Specular X-Ray Reflectivity (XRR) was performed on the film and data were analyzed using a two-layer model SiO2/Si substrate. The XRR determined film density of 2.08 g/cc. The deposited film has composition of 67.3% O and 32.7% Si as detected by XPS. There is no carbon or nitrogen detected in the film.

Example 9

Atomic Layer Deposition of Silicon-containing Films Using Oxygen Plasma Process Atomic layer depositions of silicon-containing films were conducted using dimethoxy(cis-2,6-dimethylpiperidino)silane and oxygen plasma on 300 mm Si wafer. The depositions were performed on a production PEALD tool, ASM Stellar 3000. The precursor was delivered at room temperature using 500 sccm of Ar gas. All gas and chemical delivery lines were heated to 100° C. while substrate temperature is set to 300° C. Chamber pressure was set to 3 Torr. Deposition was performed using oxygen plasma as oxygen source using the following steps:

Step 1. Precursor with Ar carrier gas and oxygen are introduced into the chamber simultaneously for 1 to 4 seconds Step 2. Precursor flow is stopped while Ar and oxygen are keep flowing into the chamber for 1 second.

Step 3. Plasma with power of 200 W, to activate oxygen, is turned on for 2 seconds.

Step 4. Plasma is turned off for 1 second

Steps 1 through 4 are repeated to achieve a desired thickness as shown in Table 2.

TABLE 2

Summary of Resulting Silicon-containing Films dimethoxy(cis-2,6-dimethylpiperidino)silane using oxygen plasma process at 300° C.

| Precursor pulse (sec) | Thickness (Å) | Deposition Rate (Å/cycle) | Ref. index |
|---|---|---|---|
| 1 | 724 | 1.0 | 1.46 |
| 2 | 551 | 1.1 | 1.46 |
| 4 | 375 | 1.1 | 1.48 |

Non-uniformity for the deposited films is less than 3% across 300 mm wafers. The films consist of 66% O and 34% Si with density of 2.09 g/cc as measured by XPS and XRR respectively. XPS does not detect any carbon or nitrogen in the films.

The working example and embodiments of this invention listed above, are exemplary of numerous embodiments that may be made of this invention. It is contemplated that numerous materials other than those specifically disclosed may be made. Numerous other configurations of the process may also be used, and the materials used in the process may be elected from numerous materials other than those specifically disclosed.

The invention claimed is:

1. An alkoxyaminosilane for depositing a silicon-containing film selected from the group consisting of di-ethoxy(tert-butylamino)methylsilane, diethoxy(tert-pentylamino)methylsilane, diethoxy(iso-propoxyamino)methylsilane, diethoxy(tert-butylamino)methylsilane, diethoxy(tert-pentylamino)methylsilane, diethoxy(iso-propoxyamino)methylsilane, di-tert-butoxy(methylamino)methylsilane, di-tert-butoxy(ethylamino)methylsilane, ditert-butoxy(iso-propylamino)methylsilane, di-tert-butoxy(n-butylamino)methylsilane, di-tert-butoxy(sec-butylamino)methylsilane, di-tert-butoxy(iso-butylamino)methylsilane, di-tert-butoxy(tert-butylamino)methylsilane, di-tert-pentoxy(methylamino)methylsilane, di-tert-pentoxy(ethylamino)methylsilane, di-tert-pentoxy(iso-propylamino)methylsilane, di-tert-pentoxy(n-butylamino)methylsilane, di-tert-pentoxy(sec-butylamino)methylsilane, di-tert-pentoxy(iso-butylamino)methylsilane, di-tert-pentoxy(tert-butylamino)methylsilane, dimethoxy(phenylmethylamino)methylsilane, and diethoxy(phenylmethylamino)methylsilane.

2. A deposition process for depositing a silicon-containing film using at least one precursor comprising an alkoxyaminosilane selected from the group consisting of di-ethoxy(tert-butylamino)methylsilane, diethoxy(tert-pentylamino)methylsilane, diethoxy(iso-propoxyamino)methylsilane, diethoxy(tert-butylamino)methylsilane, diethoxy(tert-pentylamino)methylsilane, diethoxy(iso-propoxyamino)methylsilane, di-tert-butoxy(methylamino)methylsilane, di-tert-butoxy(ethylamino)methylsilane, ditert-butoxy(iso-propylamino)methylsilane, di-tert-butoxy(n-butylamino)methylsilane, di-tert-butoxy(sec-butylamino)methylsilane, di-tert-butoxy(iso-butylamino)methylsilane, di-tert-butoxy(tert-butylamino)methylsilane, di-tert-pentoxy(methylamino)methylsilane, di-tert-pentoxy(ethylamino)methylsilane, di-tert-pentoxy(iso-propylamino)methylsilane, di-tert-pentoxy(n-butylamino)methylsilane, di-tert-pentoxy(sec-butylamino)methylsilane, di-tert-pentoxy(iso-butylamino)methylsilane, di-tert-pentoxy(tert-butylamino)methylsilane, dimethoxy(phenylmethylamino)methylsilane, and diethoxy(phenylmethylamino)methylsilane.

3. The process of claim 2, wherein the deposition process is selected from the group consisting of cyclic CVD (CCVD), MOCVD (Metal Organic CVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, deposition from supercritical fluids, and low energy CVD (LECVD), and flowable chemical vapor deposition.

4. The process of claim 2, wherein the deposition process further comprises a nitrogen source selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixture thereof.

5. The process of claim 2, wherein the deposition process further comprises an oxygen source selected from the group consisting of water ($H_2O$) (e.g., deionized water, purifier water, and/or distilled water, a mixture containing water and other organic liquid), oxygen ($O_2$), oxygen plasma, ozone ($O_3$), NO, $NO_2$, water plasma, carbon monoxide (CO), carbon dioxide ($CO_2$) and combinations thereof.

6. The process of claim 2, wherein the deposition process is selected from the group consisting of atomic layer deposition (ALD), plasma enhanced ALD (PEALD), and plasma enhanced cyclic CVD (PECCVD) process.

7. The process of claim 2, wherein the deposition process is flowable chemical vapor deposition (FCVD).

8. A vessel which is used to deliver a precursor for the deposition of a silicon-containing film, the vessel comprising the precursor selected from the group consisting of di-ethoxy(tert-butylamino)methylsilane, diethoxy(tert-pentylamino)methylsilane, diethoxy(iso-propoxyamino)methylsilane, diethoxy(tert-butylamino)methylsilane, diethoxy(tert-pentylamino)methylsilane, diethoxy(iso-propoxyamino)methylsilane, di-tert-butoxy(methylamino)methylsilane, di-tert-butoxy(ethylamino)methylsilane, ditert-butoxy(iso-propylamino)methylsilane, di-tert-butoxy(n-butylamino)methylsilane, di-tert-butoxy(sec-butylamino)methylsilane, di-tert-butoxy(iso-butylamino)methylsilane, di-tert-butoxy(tert-butylamino)methylsilane, di-tert-pentoxy(methylamino)methylsilane, di-tert-pentoxy(ethylamino)methylsilane, di-tert-pentoxy(iso-propylamino)methylsilane, di-tert-pentoxy(n-butylamino)methylsilane, di-tert-pentoxy(sec-butylamino)methylsilane, di-tert-pentoxy(iso-butylamino)methylsilane, di-tert-pentoxy(tert-butylamino)methylsilane, dimethoxy(phenylmethylamino)methylsilane, diethoxy(phenylmethylamino)methylsilane; and wherein the purity of the precursor is about 98% or greater.

9. The vessel of claim 8 wherein the vessel is comprised of stainless steel.

10. A composition for the deposition of a dielectric film comprising:

an alkoxyaminosilane selected from the group consisting of di-ethoxy(tert-butylamino)methylsilane, diethoxy(tert-pentylamino)methylsilane, diethoxy(iso-propoxyamino)methylsilane, diethoxy(tert-butylamino)methylsilane, diethoxy(tert-pentylamino)methylsilane, diethoxy(iso-propoxyamino)methylsilane, di-tert-butoxy(methylamino)methylsilane, di-tert-butoxy(ethylamino)methylsilane, ditert-butoxy(iso-propylamino)methylsilane, di-tert-butoxy(n-butylamino)methylsilane, di-tert-butoxy(sec-butylamino)methylsilane, di-tert-butoxy(iso-butylamino)methylsilane, di-tert-butoxy(tert-butylamino)methylsilane, di-tert-pentoxy(methylamino)methylsilane, di-tert-pentoxy(ethylamino)methylsilane, di-tert-pentoxy(iso-propylamino)methylsilane, di-tert-pentoxy(n-butylamino)methylsilane, di-tert-pentoxy(sec-butylamino)methylsilane, di-tert-pentoxy(iso-butylamino)methylsilane, di-tert-pentoxy(tert-butylamino)methylsilane, dimethoxy(phenylmethylamino)methylsilane, and diethoxy(phenylmethylamino)methylsilane; and a silicon precursor selected from the group consisting of bis(tert-butylamino)silane (BTBAS), bis(diethylamino)silane (BDEAS), di-iso-propylaminosilane (DIPAS), di-sec-butylaminosilane (DSBAS), tris(dimethylamino)silane (TRDMAS), tetraethoxysilane (TEOS), triethoxysilane (TES), di-tert-butoxysilane (DTBOS), di-tert-pentoxysilane (DTPOS), methyltriethoxysilane (MTES), tetramethoxysilane (TMOS), trimethoxysilane (TMOS), methyltrimethoxysilane (MTMOS), di-tert-butoxymethylsilane, di-tert-butoxyethylsilane, di-tert-pentoxymethylsilane, and di-tert-pentoxyethylsilane.

* * * * *

UNITED STATES PATENT AND TRADEMARK OFFICE
CERTIFICATE OF CORRECTION

PATENT NO. : 9,677,178 B2  
APPLICATION NO. : 14/940249  
DATED : June 13, 2017  
INVENTOR(S) : Daniel P. Spence et al.

Page 1 of 1

It is certified that error appears in the above-identified patent and that said Letters Patent is hereby corrected as shown below:

In the Claims

Column 22, Line 36, in Claim 1:  
Delete the word "diethoxy(iso-propoxyamino)methylsilane" and insert the word  
-- diethoxy(iso-propylamino)methylsilane --.

Signed and Sealed this  
Second Day of April, 2019

Andrei Iancu  
*Director of the United States Patent and Trademark Office*